US00PP11979P2

(12) United States Plant Patent
Moon

(10) Patent No.: US PP11,979 P2
(45) Date of Patent: Jul. 3, 2001

(54) DEODAR CEDAR TREE NAMED 'CDMTF1'

(75) Inventor: Dwayne C. Moon, Loganville, GA (US)

(73) Assignee: Tree Introductions, Inc., Athens, GA (US)

( * ) Notice: Subject to any disclaimer, the term of this patent is extended or adjusted under 35 U.S.C. 154(b) by 0 days.

(21) Appl. No.: 09/359,519

(22) Filed: Jul. 23, 1999

(51) Int. Cl.[7] ..... A01H 5/00
(52) U.S. Cl. ..... Plt./213

(58) Field of Search ..... Plt./213

*Primary Examiner*—Bruce R. Campell
*Assistant Examiner*—Kent L. Bell
(74) *Attorney, Agent, or Firm*—Klarquist Sparkman Campbell Leigh & Whinston LLP

(57) ABSTRACT

A Deodar Cedar tree named 'CDMTF1' having an upright, narrow growth habit with a dense foliage canopy, a dominant leader, branches which generally ascend upwardly from the trunk or leader, silvery green needles and which is also capable of being reproduced reliably from vegetative cuttings.

3 Drawing Sheets

DESCRIPTION

The present invention relates to a new and distinct variety of *Cedrus deodara*, Deodar Cedar, which has been given the varietal name 'CDMTF1'.

I discovered my new tree in 1995 as a chance seedling (parantage unknown) of Deodar Cedar growing in a cultivated area in a nursey in Walton County, Ga. This new variety originated as a seedling planted in the spring of 1991. As I observed the initially discovered tree of my new variety, the uniqueness of this tree became apparent because of its narrow, upright growing habit and its closely spaced, ascending branches. This new tree distinguishes itself from other Deodar Cedars known to the inventor by virtue of its narrow, upright habit and the dense uniformity and uprightness of its branches. In 1998, the initially discovered tree of my new variety was asexually propagated by softwood cuttings at the Moon Tree Farm in Walton County, Ga., and the progeny have proven to be true to the type and retain the narrow, upright habit and branching characteristics of the initially discovered tree even as smaller plants.

I observed this tree of my new variety for a period of time and believe it is particularly useful in landscape settings where upright, tight evergreen tree forms are important, such as in proximity to buildings or in restricted spaces or in any situation where fast-growing, consistent screens are needed as windbreaks or as control for noise pollution, especially in urban areas where space is at a premium.

In contrast, cultivated Deodar Cedar is largely represented in the industry by seedling material, although there are approximately fifty different forms that have been recognized. Seedling Deodar Cedar is widely variable in growth habit, but typically display the graceful pendulous branching that typifies the species.

There are a few Deodar Cedar cultivars which have dense or upright habits. 'Descanso Dwarf' is an upright and compact plant which has bright green foliage but semi-pendulous branching. 'Deep Cove' is an upright growing, pyramidal shaped tree with dense foliage that emerges a stark white. 'Blue Snake' is an extremely upright plant with sparse, weeping branches. These three cultivars are commercially available and are, insofar as known by the inventor, not patented. It is notable that these cultivars described as dense are also slower growing and typically more shrub-like in habit. The tree forms of typical Deodar Cedar are usually less dense and wide-spreading.

My new tree has a narrow, upright, dense habit with branches that generally ascend upwardly from the trunk or leader of the tree. To my knowledge, this growth habit is not represented by an other known Deodar Cedar cultivar or seedling.

Commonly, Deodar Cedar trees are typically large evergreen trees that mature between forty to seventy feet high and nearly as wide. As a young tree, these Deodar Cedar trees are broadly pyramidal with pendulous branches, but age into a wide-spreading, more open tree. Deodar Cedar is a popular evergreen tree because of its broad-spreading habit and slightly weeping branches. There is, however, a need for a narrow, upright form that will lend itself to growing situations where space is limited. Consequently, a new variety of Deodar Cedar which has a narrow, upright habit and closely spaced, upright branches, would be particularly useful.

My new variety has been asexually propagated from softwood cuttings at my direction. This propagation and observation of the resulting progeny have proven the characteristics of my new variety to be firmly fixed and true to the type. Furthermore, these observations have confirmed that my new variety represents a new and improved variety of Deodar Cedar as particularly evidenced by its unique dense, narrow, upright growth habit and generally upwardly ascending branches. My new variety has proven that it can reliably be asexually propagated using vegetative propagation techniques.

The accompanying photographs depict the color of the tree and doliage of my new variety as nearly true as is reasonably possible to make the same in a color illustration of this character.

My 'CDMTF1' variety of Deodar Cedar tree is currently being grown in Walton County, Ga. The initially discovered tree of my new variety was found in and is growing in an area of Walton County that has a clay-loam soil type. Walton County is in upper USDA Zone 7 and receives an average yearlyl rainfall of around fifty inches. My new tree has not been observed under all growing conditions, and thus variations may occur as a result of different growing conditions. Color often varies in a plant under certain growing conditions. The following is a detailed description of my new variety of Deodar Cedar with color terminology in accordance with The Royal Horticultural Society (R.H.S.) Colour Chart published by The Royal Horticultural Society of London. The observations set forth are of the initially discovered tree growing in Walton County, Ga. at about age seven and one-half years old and of progeny thereof which, unless otherwise specified, are about one and one-half years old.

Figure 1:
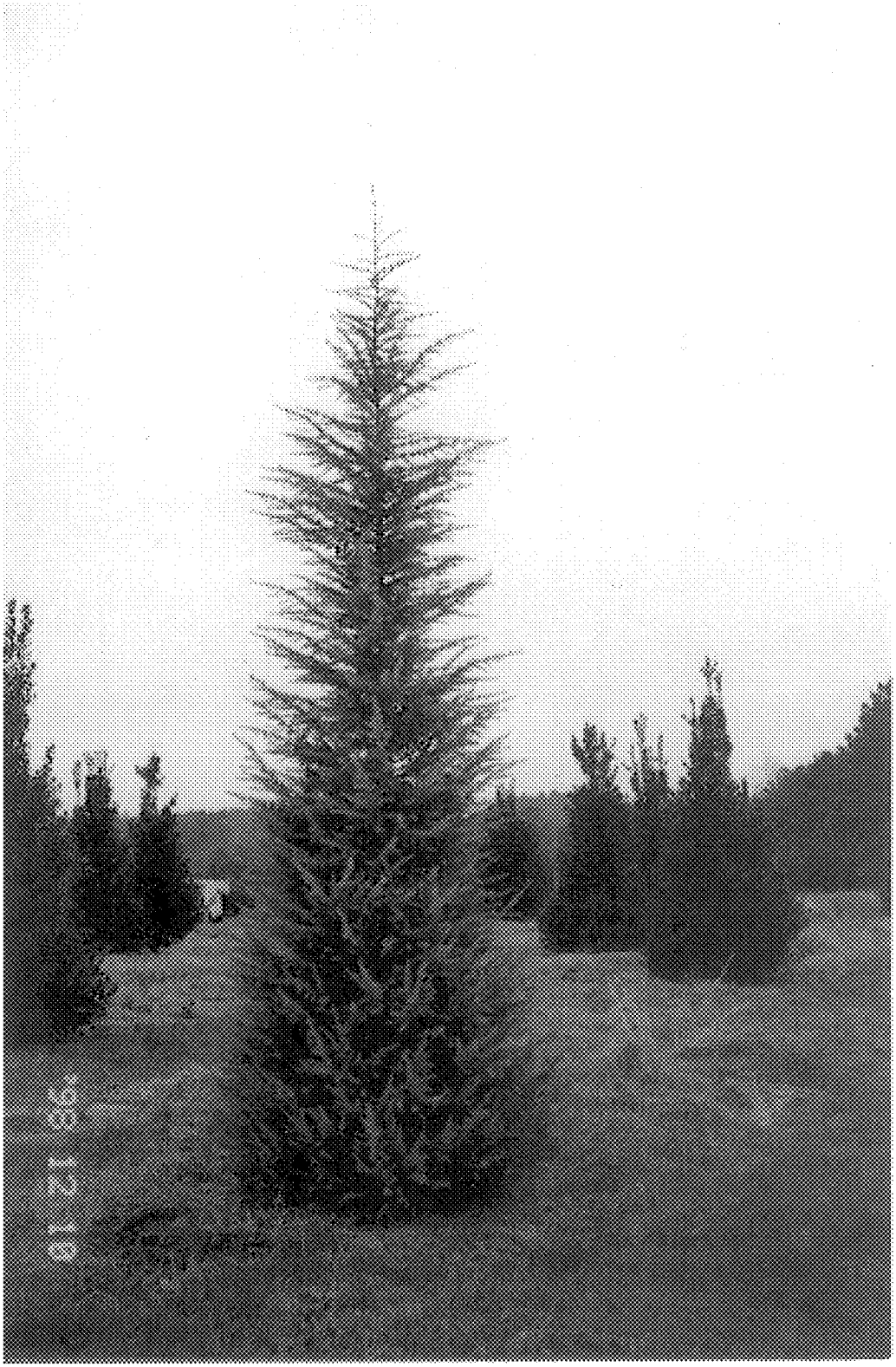
FIG. 1 is a photograph of an entire tree of my new variety.

My new variety of Deodar Cedar is characterized by a uniform upright habit and closly spaced upwardly ascending branching (FIG. 1). It is also a fast grower. The initially discovered tree has averaged at least about two feet of growth per year since it was planted. In December 1998, the initially discovered tree was eighteen feet high and seven feet wide, with a height to width ratio of 2.57. This upright compact form with dense foliage and upright branching distinguishes my new variety from typical *Cedrus deodara* trees known to the inventor. Most Deodar Cedars are broadly pyramidal to wide spreading and flat-topped.

My new tree maintains a tight, upright branching pattern which contributes to its narrow-columnar habit. In contrast, seedlings and some other cultivars which I have observed do not maintain this narrow habit. To my knowledge, no other Deodar Cedars have this narrow habit and dense, upright branching. The unique growth habit of this new variety insures its capacity for use in areas where growing space is restricted, particularly along streets with buildings or sites which will not accommodate a broader canopy and as a screen or hedge where space is limited.

My new variety is distinctly different from 'Descanso Dwarf' in that my new variety does not have pendulous branching. My new variety is also distinctly different from 'Deep Cove' in that my new variety is much less pyramidal and more upright in it branching with no white variegation. My new variety is also distinctly different from 'Blue Snake' in that my new variety is much denser and does not have weeping branching, nor does it have the same bluish needle color of 'Blue Snake'.

My new tree has a branching habit and dendritic pattern of a single leader (bole). Secondary branches at the base of the tree tend to emerge at about eighty to ninety degree angles to the main trunk and tend to sweep upward to fifty degree angles. Secondary branches at the top of the tree tend to emerge at about fifty degree angles to the main leader and tend to sweep upwardly to a thirty to forty degree angle. Branches are uniformly and densely borne around the central leader with no large gaps from one branch insertion to the next. As a result, as can be seen from FIG. 1, the tree of my new variety is uniformly branched and symmetrical with a dense canopy. In contrast, traditional seedling Deodar Cedars and most of the cultivars are usually more open and in youth must be pruned to produce an upright habit and generally become more open with age. Most Deodar Cedars also have pendulous branching and nearly horizontal branch angles.

The lower trunk and larger branches are typical of the species, exhibiting the same silvery, glaucous appearance of most Deodar Cedars.

The needles are typical of the species and most other cultivars, being glabrous green beneath and silvery green above, the silver hue coming from the waxy bloom that is most prominent on the youngest needles. The needle color at the tip of a branch is silvery green (upper surface RHS 133D). The mature needle is smaller than that of the species, averaging one inch to one and one-half inches long, and one-sixteenth inch wide. The needles are borne in a whorl of ten to fifteen needles on the current season' growth. The needles are striated and somewhat twisted or spiraled. The needles have an acute apex. The undersides of the leaves are glabrous, and greener than the upper side of the needle (undersides RHS 137B). There is no pubescence present on any parts of the needles.

The stems of my new variety are typical of the species. Stem color is best described as a greyed-green (RHS 197B), becoming striated with age, and finally greying to the same color as the trunk (RHS 198C to RHS 197B).

My new variety has not been observed to have any pollen or cones yet. Whether the new variety is self fertile is not yet known.

THE PLANT

Parentage: Initially discovered tree is a chance Deodar Cedar seedling of an unknown parentage growing in a cultivated area of a nursery in Walton County, Ga.

Tree shape: Narrow, upright conical (FIG. 1). Ultimate height and width of the tree is unknown.

Trunk: Dominant central leader, greyed-green in color (RHS 198C to RHS 197B), typical of the species. The initially discovered tree measured at about six inches above the ground has a diameter of about five and one-fourth inches. Two year old progeny of the variety measured at about six inches above the ground have a diameter of about one and one-fourth inches. These measuements were taken from trees growing in a nursery in Georgia.

Figure 2:
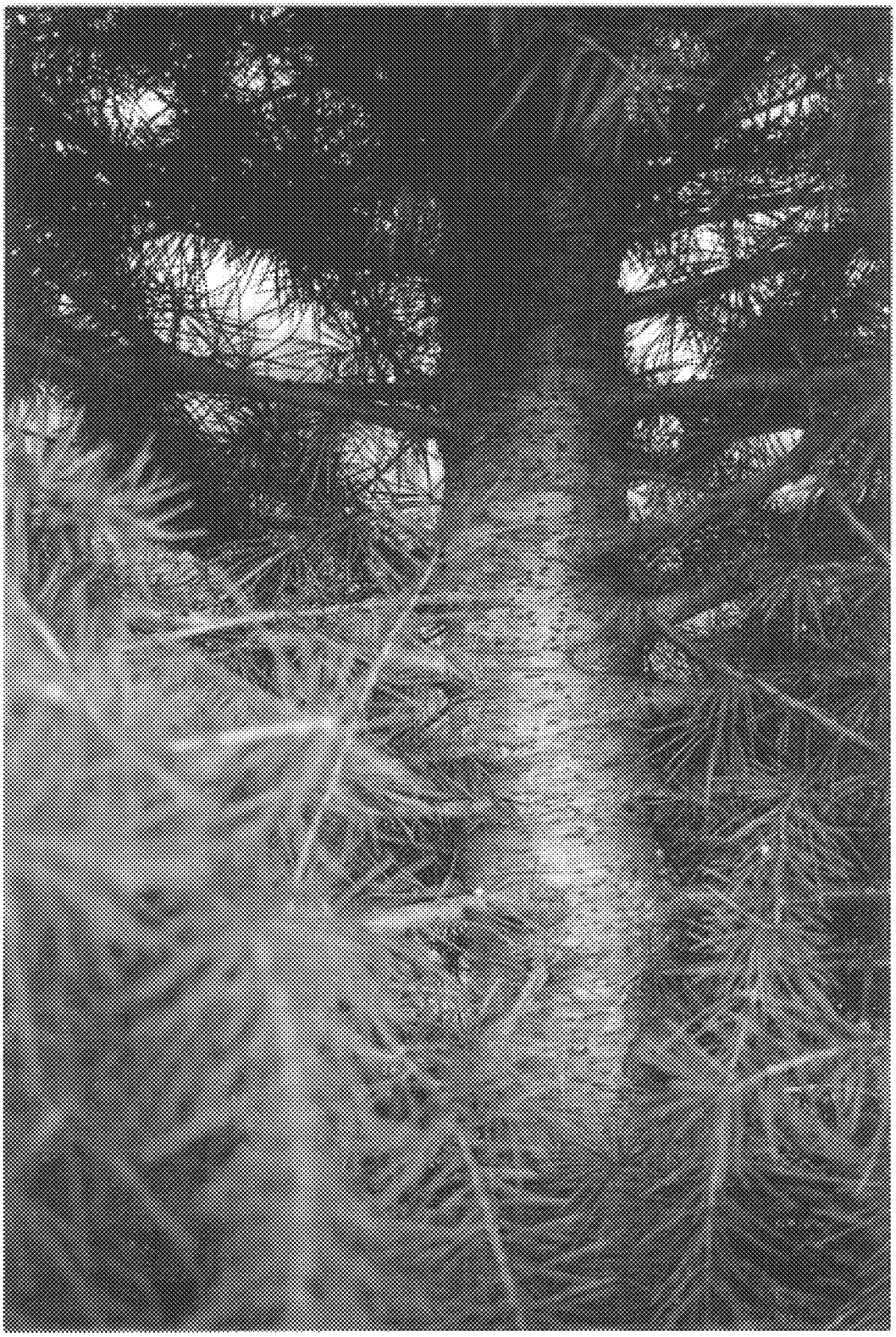
FIG. 2 is a close-up of a trunk of my new variety showing mature bark and also showing its dense branching habit.

Bark: Smooth, greyed-green (RHS 197B). Typical of the species. Mature bark color: (Observed in the initially discovered tree) Greyed-green (RHS 197B), typical of the species (FIG. 2).

Branches: Ascending. Branches along the lower portion of the trunk tend to emerge from the dominant leader at an angle of about eighty to ninety degrees (base) and sweeping upwardly to a fifty degree angle. Branches emerging from the main leader at an upper portion thereof tend to emerge at an angle of about fifty degrees and sweep upward to thirty to forty degrees (base) (FIG. 1). The difference in angles between upper and lower branches may be due to the effect of gravity on the branches over time. Branches of the initially discovered tree measured at about three feet above the ground are about three and one half feet long and about three-fourths of an inch in diameter. Branches of two year old progeny of my new variety measured at about three feet above the ground are about one foot long and one-tenth of an inch in diameter. Branches of the two year old progeny measured about six feet above the ground are about four inches long and less than one-tenth of an inch in diameter. These measurements were taken from trees growing in a nursery in Georgia.

Leaves: Leaf shape is needle-like, rounded to somewhat flattened in cross-section, typical of the species although somewhat smaller. Arrangement is whorled (FIG. 3).

*Leaf surface*.—Upper leaf surface of recent growth has a waxy bloom that imparts a silver color to the upper side of the needles (RHS 133D). The lower surface is glabrous and green (RHS 137B) (FIG. 3).

Figure 3:
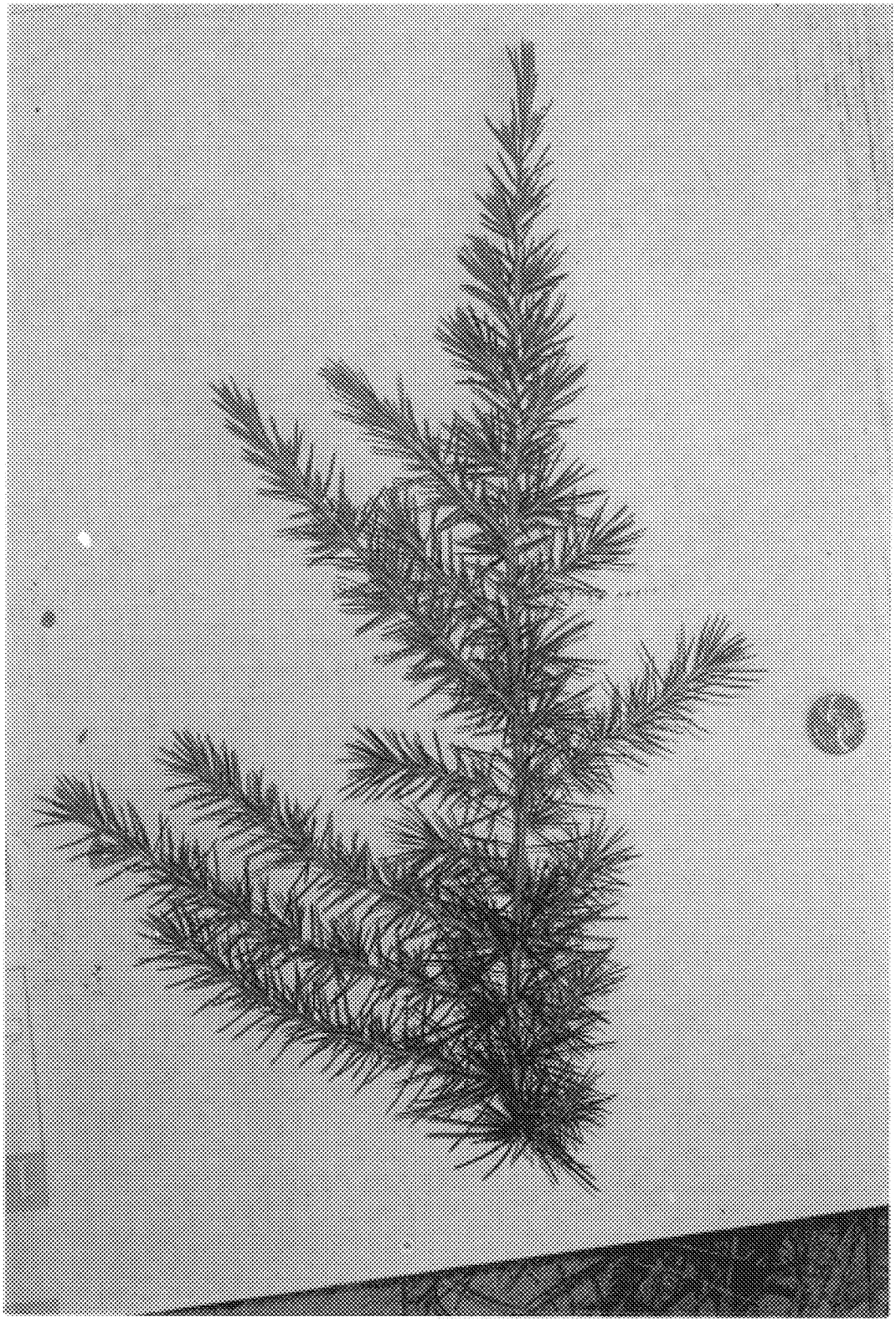
FIG. 3 is a close-up of a limb from a tree of my new variety showing the needle color and needle arrangement.

*Leaf size*.—Leaves average 1 to 1½ inches long, 1/16 inches wide, ten to fifteen needles per whorl (FIG. 3).

Pollen and cones: Initially discovered tree and progeny have not yet produced pollen or cones.

Pest and disease resistance: No susceptibility to pests or disease has been observed.

Winter hardiness: No available information, although the initially discovered tree has been exposed to winter temperatures which unofficially reached a low of about 4° F.

I claim:

1. A new and distinct variety of Deodar Cedar tree substantially as herein shown and described, characterized particularly as to novelty by its upright dense growth habit and branches which generally extend upwardly from the trunk of primary leader of the tree.

* * * * *

UNITED STATES PATENT AND TRADEMARK OFFICE

CERTIFICATE OF CORRECTION

PATENT NO. : PP 11,979 P2
DATED : July 3, 2001
INVENTOR(S) : Dwayne C. Moon

It is certified that error appears in the above-identified patent and that said Letters Patent is hereby corrected as shown below:

Column 3,
Line 6, the word “yearlyl” should be -- yearly --

Column 6,
Line 10, the phrase “trunk of primary” should be -- trunk or primary --

Signed and Sealed this

Fourth Day of June, 2002

*Attest:*

*Attesting Officer*

JAMES E. ROGAN
*Director of the United States Patent and Trademark Office*